United States Patent [19]

Dorward et al.

[11] Patent Number: 5,217,872

[45] Date of Patent: Jun. 8, 1993

[54] **METHOD FOR DETECTION OF *BORRELIA BURGDORFERI* ANTIGENS**

[75] Inventors: David W. Dorward; Tom G. Schwan; Claude F. Garon, all of Hamilton, Mont.

[73] Assignee: The United States of America as represented by the Department of Health and Human Services, Washington, D.C.

[21] Appl. No.: 485,551

[22] Filed: Feb. 27, 1990

[51] Int. Cl.$^5$ .......................................... G01N 33/569
[52] U.S. Cl. .................................. 435/7.32; 435/7.92; 435/975; 436/547; 436/548; 530/388.4; 530/389.5; 530/391.3
[58] Field of Search ................. 435/7.32, 7.92, 7.94, 435/29, 968, 971, 975; 436/547, 548, 518, 800, 804, 808, 828; 530/387, 388.4, 389.5, 391.1, 391.3

[56] References Cited

U.S. PATENT DOCUMENTS 4,313,734 2/1982 Leuvering ........................... 436/525
4,888,276 12/1989 Shelburne ........................... 435/7.32

OTHER PUBLICATIONS

Perng et al, Infection and Immunity, 59(6):2070-2074 (Jun. 1991).
Dorward et al, Infection and Immunity, 60(3):838-844 (Mar. 1992).
Garon et al, "Structural features of *Borrelia burgderferi*-The Lyme Disease spirochete: silver staining for nucleic acids" Scanning Microscopy Supplement 3 (1989) pp. 109-115.
Bissett et al, "An unusual isolate of *Borrelia burgdorferi* from a tick in California" Annals of The New York Academy of Sciences 539:369-371 (1988).
Voller et al "Enzyme-linked immunosorbent assay" in Manual of Clinical Laboratory Immunology pp. 99-109 (1986).
Journal of Clinical Microbiology, vol. 28, No. 7, Jul./1990, LeFebvre et al., "The 83-kilodalton antigen of *Borrelia burgdorferi* which stimulates immoglobulin M(IgM) and IgG responses in infected hosts is expressed by a chromosomal gene" pp. 1763-1675.
Journal of Clinical Investigation, vol. 78, Oct./1986, Craft et al., "Antigens of *Borrelia burgdorferi* recognized during Lyme Disease," pp. 934-939.
Infection and Immunity, vol. 54, No. 1, Oct./1986, Howe et al., "Organization of genes encoding two outer membrane proteins of the Lyme Disease agent *Borrelia burgdorferi* within a single transcriptional unit," pp. 207-212.

*Primary Examiner*—Esther L. Kepplinger
*Assistant Examiner*—Carol E. Bidwell
*Attorney, Agent, or Firm*—Morgan & Finnegan

[57] ABSTRACT

The invention relates to novel antigens associated with *Borrelia burgdorferi* which are exported (or shed) in vivo and whose detection is a means of diagnosing Lyme disease. The antigens are extracellular membrane vesicles and other bioproducts including the major extracellular protein. The invention further provides antibodies, monoclonal and/or polyclonal, labeled and/or unlabeled, that react with the antigens. The invention is also directed to a method of diagnosing Lyme disease by detecting the antigens in a biological sample taken from a host using the antibodies in conventional immunoassay formats. The invention further relates to kits, for the diagnosis of Lyme disease, comprising the antibodies and ancillary reagents. The advantage of the antibodies used in the invention is that they react with the antigens from geographically diverse strains of *Borrelia burgdorferi*, but do not react with antigens from related *Borrelia* spirochetes.

26 Claims, 6 Drawing Sheets

METHOD FOR DETECTION OF *BORRELIA BURGDORFERI* ANTIGENS

FIELD OF THE INVENTION

The present invention relates to novel antigens associated with *Borrelia burgdorferi*, antibodies that are raised against the antigens and the use of the antibodies to diagnose Lyme disease.

BACKGROUND OF THE INVENTION

The immunological interactions between the Lyme disease spirochete, *Borrelia burgdorferi*, and its mammalian hosts are poorly understood (Bosler, E. M., D. P. Cohen, L. Schulze, C. Olsen, W. Benard, and B. Lissman. 1988. Host responses to *Borrelia burgdorferi* in dogs and horses, p. 221-234. In J. L. Benach, and E. M. Bosler (eds.), Lyme disease and related disorders. Annals of the New York Academy of Sciences 539; Dlesk, A., D. F. Bjarnason, P. Mitchell, and P. McCarty. 1988. Lyme disease presenting as seronegative rheumatoid arthritis, p. 454-455. In J. L. Benach, and E. M. Bosler (eds.), Lyme disease and related disorders. Annals of the New York Academy of Sciences 539; Duray, P. H., and A. C. Steere. 1988. Clinical pathologic correlations of Lyme disease by stage, p. 65-79. In J. L. Benach, and E. M. Bosler (eds.), Lyme disease and related disorders. Annals of the New York Academy of Sciences 539; Fox, J. L. 1989. Interest in Lyme disease grows. ASM News 55:65-66; Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58-61; Magnarelli, L. A. 1988. Serologic diagnosis of Lyme disease, p. 154-161. In J. L. Benach, and E. M. Bosler (eds.), Lyme disease and related disorders. Annals of the New York Academy of Sciences 539; Schwan, T. G., W. Burgdorfer, and C. F. Garon. 1988. Changes in infectivity and plasmid profile of the Lyme disease spirochete, *Borrelia burgdorferi*, as a result of in vitro cultivation. Infect. Immun. 56:1831-1836; schwan, T. G., W. Burgdorfer, M. E. Schrumpf, and R. H. Karstens. 1988. The urinary bladder, a consistent source of *Borrelia burgdorferi* in experimentally infected white-footed mice (*Peromyscus leucopus*). J. Clin. Microbiol. 26:893-895; Sticht-Groh, V., R. Martin, and I. Schmidt-Wolf. 1988. Antibody titer determinations against *Borrelia burgdorferi* in blood donors and in two different groups of patients, p. 497-499. In J. L. Benach, and E. M. Bosler (eds.), Lyme disease and related disorders. Annals of the New York Academy of Sciences 539; Stiernstedt, G., R. Gustafsson, M. Kaarlsson, B. Svenungsson, and B. Skoldenberg. 1988. Clinical manifestations and diagnosis of neuroborreliosis, p. 46-55. In J. L. Benach, and E. M. Bosler (eds.), Lyme disease and related disorders. Annals of the New York Academy of Sciences 539 and Wilske, B., V. Preac-Mursic, G. Schierz, R. Kuhbeck, A. G. Barbour, and M. Kramer. 1988. Antigenic variability of *Borrelia burgdorferi*. p. 126-143. In. J. L. Benach, and E. M. Bosler (eds.), Lyme disease and related disorders. Annals of the New York Academy of Sciences 539). Most mammalian hosts mount an antibody response to the spirochete, however the antibodies are often serologically cross-reactive with other species of Borrelia, and individuals with sero-negative infections have been encountered using standard screening criteria (Dlesk, A., D. F. Bjarnason, P. Mitchell, and P. McCarty. 1988. Lyme disease presenting as seronegative rheumatoid arthritis, p. 454-455. In J. L. Benach, and E. M. Bosler (eds.), Lyme disease and related disorders. Annals of the New York Academy of Sciences 539; Fox, J. L. 1989. Interest in Lyme disease grows. ASM News 55:65-66; Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58-61; Magnarelli, L. A. 1988. Serologic diagnosis of Lyme disease, p. 154-161. In J. L. Benach, and E. M. Bosler (eds.), Lyme disease and related disorders. Annals of the New York Academy of Sciences 539; Sticht-Groh, V., R. Martin, and I. Schmidt-Wolf. 1988. Antibody titer determinations against *Borrelia burgdorferi* in blood donors and in two different groups of patients, p. 497-499. In J. L. Benach, and E. M. Bosler (eds.), Lyme disease and related disorders. Annals of the New York Academy of Sciences 539 and Wilske, B., V. Preac-Mursic, G. Schierz, R. Kuhbeck, A. G. Barbour, and M. Kramer. 1988. Antigenic variability of *Borrelia burgdorferi*. p. 126-143. In. J. L. Benach, and E. M. Bosler (eds.), Lyme disease and related disorders. Annals of the New York Academy of Sciences 539:126-143). Furthermore, strain variation among B. burgdorferi isolates, and antigenic variation within populations render immunodiagnostics, based on monoclonal antibodies, potentially insensitive and unreliable for detection of circulating and excreted antigens in some hosts Barbour, A. G., R. H. Heiland, and T. R. Howe. 1985. Heterogeneity of major proteins in Lyme disease borreliae: a molecular analysis of North American and European isolates. J. Infect. Dis. 152:478-484 and Wilske, B., V. Preac-Mursic, G. Schierz, R. Kuhbeck, A. G. Barbour, and M. Kramer. 1988. Antigenic variability of *Borrelia burgdorferi*. p. 126-143. In. J. L. Benach, and E. M. Bosler (eds.), Lyme disease and related disorders. Annals of the New York Academy of Sciences 539:126-143). Therefore, clinical symptoms, patient history, and occasional primary isolations of the spirochete from blood or tissue biopsies, provide the bases for most diagnoses (Benach, J. L., E. M. Bosler, J. P. Hanrahan, J. L. Coleman, G. S. Habicht, T. F. Bast, D. J. Cameron, J. L. Ziegler, A. G. Barbour, W. Burgdorfer, R. Edelman, and R. A. Kaslow. 1983. Spirochetes isolated from the blood of two patients with Lyme disease. N. Engl. J. Med. 308:740-742; Dlesk, A., D. F. Bjarnason, P. Mitchell, and P. McCarty. 1988. Lyme disease presenting as seronegative rheumatoid arthritis, p. 454-455. In J. L. Benach, and E. M. Bosler (eds.), Lyme disease and related disorders. Annals of the New York Academy of Sciences 539:454-455; Duray, P. H., and A. C. Steere. 1988. Clinical pathologic correlations of Lyme disease by stage, p. 65-79. In J. L. Benach, and E. M. Bosler (eds.), Lyme disease and related disorders. Annals of the New York Academy of Sciences 539:65-79 and Rawlings, J. A., P. V. Fornier, and G. J. Teltow. 1987. Isolation of Borrelia spirochetes from patients in Texas. J. Clin. Microbiol. 25:1148-1150.20). Such problems are often cited as factors influencing the reportedly poor diagnostic acumen for Lyme disease (Fox, J. L. 1989. Interest in Lyme disease grows. ASM News 55:65-66).

Considerable work is currently directed toward identifying conserved, species-specific cell surface antigens for diagnostic use, and for epidemiological and pathogenetic studies. Expression of outer surface Protein A (OspA) is considered universal among *B. burgdorferi* isolates, but not among related spirochetes (Barbour, A. G., R. H. Heiland, and T. R. Howe. 1985. Heterogeneity of major proteins in Lyme disease borreliae: a molecular analysis of North American and European isolates. J. Infect. Dis. 152:478-484; Barbour, A. G., S. L. Tessier, and W. J. Todd. 1983. Lyme disease spirochetes and ixodid tick spirochetes share a common surface antigenic determinant defined by a monoclonal antibody. Infect. Immun. 41:795-804; Bergstrom, S., V. G. Bundoc, and A. G. Barbour. 1989. Molecular analysis of linear plasmid-encoded major surface proteins, OspA and OspB, of the Lyme disease spirochaete *Borrelia burgdorferi*. Mol. Microbiol. 3:479-486; Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58-61; Magnarelli, L. A. 1988. Serologic diagnosis of Lyme disease, p. 154-161. In J. L. Benach, and E. M. Bosler (eds.), Lyme disease and related disorders. Annals of the New York Academy of Sciences 539:154-161 and Wilske, B., v. Preac-Mursic, G. Schierz, R. Kuhbeck, A. G. Barbour, and M. Kramer. 1988. Antigenic variability of *Borrelia burgdorferi*. p. 126-143. In. J. L. Benach, and E. M. Bosler (eds.), Lyme disease and related disorders. Annals of the New York Academy of Sciences 539:126-143). This protein is immunogenic, however, surface-exposed regions appear to be antigenically variable, since surface-reactive monoclonal antibodies to OspA fail to recognize some isolates Barbour, A. G., R. H. Heiland, and T. R. Howe. 1985. Heterogeneity of major proteins in Lyme disease borreliae: a molecular analysis of North American and European isolates. J. Infect. Dis. 152:478-484; Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58-61 and Wilske, B., V. Preac-Mursic, G. Schierz, Kuhbeck, A. G. Barbour, and M. Kramer. 1988. Antigenic variability of *Borrelia burgdorferi*. p. 126-143. In. J. L. Benach, and E. M. Bosler (eds.), Lyme disease and related disorders. Annals of the New York Academy of Sciences 539:126-143).

Recent experiments have shown that OspA and several other proteins are exported from *B. burgdorferi* cells in membrane vesicles (Garon, C. F., D. W. Dorward, and M. D. Corwin. 1989. Structural features of *Borrelia burgdorferi*—the Lyme disease spirochete: silver staining for nucleic acids. Scanning Microscopy Supplement 3, pages 109-115; Dorward and Garon manuscript in preparation). Indirect evidence suggests these vesicles may be produced by spirochetes in vivo providing sustained antigenic challenge to hosts maintaining a limited population of spirochetes (Fox, J. L. 1989. Interest in Lyme disease grows. ASM News 55:65-66). To determine whether *B. burgdorferi* vesicles occur in experimentally-infected mice, polyclonal rabbit sera were generated against vesicles and an 83 kilodalton (kDa), major extracellular protein (MEP). Using these reagents, a 2-stage immune electron-microscopic assay was developed for first capturing then identifying extracellular *B. burgdorferi* antigens. The study was then extended to include antigen detections in Ixodes tick, mouse, dog, and human samples. Accordingly, the present invention relates to an assay system and to the reliable and highly sensitive detection of antigens indicative of *B. burgdorferi* infections.

The closest known technology to the present invention is a diagnostic kit, produced by 3M Corp. (Fast Lyme, Cat. No. 700-500) that uses monoclonal antibodies to detect Lyme antigens in human urine samples. The kit is limited to urine samples, can provide false-negative results with geographically diverse samples, and is marginally sensitive (Hyde F. W. et al, (1989), Detection of antigen in urine of mice and humans infected with *Borrelia burgdorferi*, etiologic agent of Lyme disease, J. Clin. Microbiol. 27:58-61).

SUMMARY OF THE INVENTION

The invention relates to novel antigens associated with *Borrelia burgdorferi* which are exported (or shed) in vivo and whose detection is a means of diagnosing Lyme disease. The antigens are extracellular membrane vesicles and other bioproducts including the major extracellular protein antigen. Another object of the invention is to provide antibodies, monoclonal and/or polyclonal, labeled and/or unlabeled, that are raised against the antigens. A further object of the invention is to provide a method of diagnosing Lyme disease by detecting the antigens in a biological sample taken from a host using the antibodies in conventional immunoassay formats. Another object of the invention is to provide kits, for the diagnosis of Lyme disease, comprising the antibodies and ancillary reagents. The advantage of the antibodies used in the invention is that they react with the antigens from geographically diverse strains of *Borrelia burgdorferi*, but do not react with antigens from related Borrelia spirochetes.

DETAILED DESCRIPTION OF THE INVENTION

Figure 1:
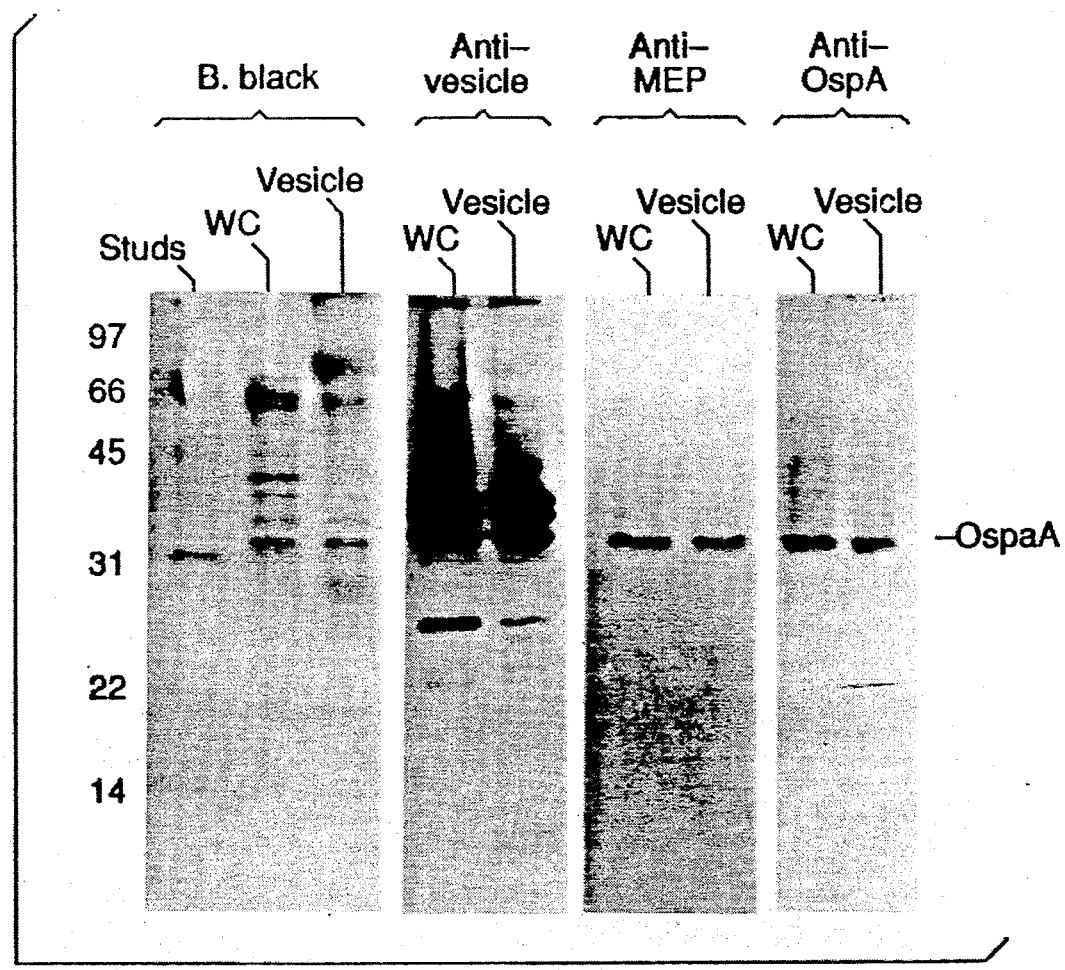
FIG. 1 shows immunoblot analysis of antibodies used for the capture and detection of *B. burgdorferi* antigens.

Current biological and serological techniques for diagnosing *Borrelia burgdorferi* infections are often inconclusive. In order to monitor Lyme disease, a rapid and sensitive assay was developed for *B. burgdorferi* antigens in infected hosts. Polyclonal rabbit antisera were raised against membrane vesicles, and against an 83 kilodalton (kDa) vesicle protein antigen, purified from in vitro *B. burgdorferi* cultures. Immunoglobulin G (IgG) was recovered from these sera and tested for species-specific reaction with several geographically diverse Borrelia isolates. Parlodion-coated electron microscope grids were activated with anti-vesicle F(ab')$_2$ fragments, then incubated with fluids or macerated tissues from ticks, mice, dogs, and humans. Captured antigens were assayed by immune electron microscopy using anti-83 kDa antibodies (that is, antibodies raised against the 83 kDa MEP antigen) and Protein A-colloidal gold conjugates. The results showed that Lyme spirochetes shed surface antigens which were readily detectable in urine, blood, and several organs from infected hosts. Positive mouse urine titers exceeded $1 \times 10^6$. Intact spirochetes were frequently observed on grids incubated with blood, spleen, or bladder preparations, and *B. burgdorferi* was re-isolated from all experimentally-infected mice. Immunoblot analysis confirmed the presence of extracellular antigens in positive mouse and human urine samples. These results reconfirm that *B. burgdorferi* antigens persist in a variety of host materials. Such antigens can be captured and identified with specific polyclonal antibodies, providing a sensitive assay for diagnosing and studying Lyme borreliosis.

Accordingly, the present invention relates to a sensitive immunoassay and diagnostic test kit for the detection of *B. burgdorferi*-specific antigens in ticks, mice, dogs, and humans. When the assay involves the immune capture of antigens with immobilized F(ab')$_2$ fragments, it is followed by specific antigen detection using polyclonal IgG. A reagent capable of reacting with polyclonal IgG (e.g., labeled protein A or labeled anti-polyclonal IgG antibodies) may be used during the assay. Using this assay, *B. burgdorferi* antigens and occasionally intact spirochetes were detected in ticks and mammalian urine, blood, and organs.

When the detection method involves the use of protein A, the capture antibodies must be, F(ab')$_2$ or F(ab) antibody fragments. Protein A binds to intact IgG. Either intact antibodies or the antigen binding fragments can be used. Only when protein A is used must the capture antibody be a fragment.

Antigens were captured with F(ab')$_2$ fragments generated against extracellular membrane vesicle concentrates. Initial characterizations of the anti-vesicle sera by immunoblot analysis and immune electron microscopy demonstrated that serum IgG recognized multiple cell and vesicle surface components including OspA and OspB, however, the sera also recognized some other host antigens. Anti-vesicle F(ab')$_2$ effectively concentrated and immobilized antigens from complex mixtures, and appeared to block non-specific adsorption of host material and assay reagents to coated electron microscopic grids. Because these antibodies cross-reacted with some host antigens, a second antibody was used for specific detection of *B. burgdorferi* antigens.

The detection antibody was generated against the 83 kDa MEP antigen. Surprisingly, immunoblots showed that the resulting polyclonal sera recognized OspA at 31 kDa, but had relatively weak activity with the original immunogen. Concurrent studies have shown that OspA and the MEP appear to be glycosylated with a variety of carbohydrates (Dorward and Garon, manuscript in preparation). Whether glycosylation or possible protein homology accounts for these results remains unclear. The finding that the anti-MEP IgG recognizes *B. burgdorferi* antigens at 83 kDa in mouse urine, and 11, 14, 22, 31, and 34 kDa in human urine, suggests that either common epitopes are expressed in several exported proteins, or the MEP readily dissociates into subunits or degradative products.

As with previous characterizations of anti-OspA monoclonal antibodies (Barbour, A. G., R. H. Heiland, and T. R. Howe. 1985. Heterogeneity of major proteins in Lyme disease borreliae: a molecular analysis of North American and European isolates. J. Infect. Dis. 152:478–484; Hyde, F. W., R. C. Johnson, T. J. White, and C. E. Shelburn 1989. Detection of antigen in urine of mice and humans infected with *Borrelia burgdorferi*, etiologic agent of Lyme disease. J. Clin. Microbiol. 27:58–61 and Wilske, B., V. Preac-Mursic, G. Schierz, R. Kuhbeck, A. G. Barbour, and M. Kramer. 1988. Antigenic variability of *Borrelia burgdorferi*. p. 126–143. In. J. L. Benach, and E. M. Bosler (eds.), Lyme disease and related disorders. Annals of the New York Academy of Sciences 539:126–143), the anti-MEP polyclonal IgG was species specific. Furthermore, whereas anti-OspA monoclonal antibodies invariably fail to bind some strains, this polyclonal antibody recognized all strains of *B. burgdorferi* tested, including several geographically diverse isolates. We presume that the polyclonal IgG binds to multiple epitopes on OspA and MEP. Hence, divergence among *B. burgdorferi* strains, reflected by amino acid sequence variation within these proteins, could occur without complete loss of antibody recognition.

When these reagents were used to examine experimentally-infected mice by electron microscopy, *B. burgdorferi*-derived material was detected in urine, blood, and macerated urinary bladder, spleen, liver, and brain tissues. Aggregated antigens were not observed in kidney tissue, however the relatively dense deposition of gold in kidney preparations suggests *B. burgdorferi* antigens were present. Minimal background labeling on control grids lacking antigen and on grids incubated with material from uninfected mice and humans, indicated that gold deposition in this assay was specific for *B. burgdorferi* antigens.

Intact spirochetes were observed on grids incubated with mouse blood, and with bladder and spleen tissue specimens from mice. A spirochete was also observed in 1 µl of a human urine sample, suggesting this detection system may facilitate studies of tissue involvement complicated by difficulty in demonstrating spirochetes in infected hosts (Fox, J. L. 1989. Interest in Lyme disease grows. ASM News 55:65–66).

Pre-incubation of the grids with anti-vesicle F(ab')$_2$ fragments dramatically increased the sensitivity of antigen detection, particularly in complex samples such as blood and macerated tissues. Flocculent antigen was detectable in these samples without pre-incubation, however the grids contained considerable quantities of unlabeled host material. Apparently, the F(ab')$_2$ fragments functioned both by concentrating Borrelia antigens on the grids, and blocking non-specific adsorption of eukaryotic material.

Vesicles were resolved on the surfaces of spirochetes adhering to grids incubated with infected tissues, indicating these vesicles are produced by *B. burgdorferi* in vivo. Gold-labeled, membranous vesicles were also observed in urine and blood. The majority of specific gold labeling occurred on flocculent material detected in *B. burgdorferi* cultures and all infected animals. While structurally-similar material was frequently observed on cell surfaces, its exact nature is currently unknown. Western blots showed that anti-MEP IgG and anti-OspA monoclonal antibodies have similar reactivities. Previous work showed that *B. burqdorferi* sloughs OspA from Cell surfaces (Barbour, A. G., S. L. Tessier, and W. J. Todd. 1983. Lyme disease spirochetes and ixodid tick spirochetes share a common surface antigenic determinant defined by a monoclonal antibody. Infect. Immun. 41:795–804). Together these results suggest that OspA and the MEP antigen share homology and may be components of a surface or s-layer that can be released from cell surfaces.

The detection of antigens in urine using monoclonal antibodies has recently been reported (Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58-61). The following Example 1 confirms that finding, and provides methods that may enhance the reported sensitivity of detection (Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58-61). Example 1 also shows that extracellular *B. burgdorferi* antigens occur in tissues in which spirochetes are infrequently reported (Duray, P. H. and A. C. Steere. 1988. Clinical pathologic correlations of Lyme disease by stage, p. 65-79. In J. L. Benach, and E. M. Bosler (eds.), Lyme disease and related disorders. Annals of the New York Academy of Sciences 539:65-79). Such results suggest either that large quantities of circulating antigen are deposited in these tissues, or that the antigen is secreted by a limited number of migrating spirochetes and the antigen persists in situ. The possible pathological effects of this material are unknown, however determining its nature and the mechanisms behind its deposition may lead to better a understanding of *B. burgdorferi* pathobiology. The reagents developed in Example 1 as discussed hereinbelow should facilitate such determinations.

Both the F(ab')$_2$ and IgG preparations proved stable when stored as lyophilized powder. In these experiments the reagents were rehydrated just prior to use, indicating appropriate preparations could be stored and distributed in aliquots for use as needed. Combining immune capture with polyclonal antigen detection should reduce false-negative detection of *B. burgdorferi*, resulting from minor antigenic variation, and enable reliable demonstrations of this spirochete and its products in vector, reservoir host, domestic animal, and human urine, blood, or tissue samples. Although designed initially for careful electron microscopic examination of captured antigens, the system is readily adaptable to more common clinical analysis protocols.

These clinical analysis protocols are well known in the art. The antibodies, particularly those raised against the MEP antigen, can be used in all the conventional immunoassay formats to detect the antigens in biological samples, and thus detect the presence of *Borrelia burgdorferi*. Both homogeneous and heterogeneous immunoassays may be used. The anti-MEP antibody can be directly labeled with conventional labels, i.e., enzymes, radioisotopes, fluorophores, colloidal metals (gold), or these labels can be attached to antibody binding proteins (anti-anti-MEP antibodies, protein A, etc.) to indirectly label the anti-MEP antibody. A preferred method of detecting the exported antigens is as follows. The anti-vesicle antibodies are bound to an inert solid substrate. The biological sample is brought into contact with this substrate under conditions conducive for the formation of immune complexes between the anti-vesicle antibodies and any antigens associated with *Borrelia burgdorferi* antigens in the sample. These antigens include the intact *Borrelia burgdorferi* spirochete, the extracellular membrane vesicles, and the exported proteins from the surface of the spirochete, including the 83 kDa MEP, and the 11, 14, 22, 31 and 34 kDa exported proteins found in human urine as described in Example 1. The substrate is washed and then brought into contact with anti-MEP antibodies under condition conducive to form a ternary sandwich immune complex consisting of an anti-vesicle(antigen)anti-MEP complex. The anti-MEP antibody can be directly labeled (see above) in which case the sandwich immune complex is directly detected. Alternatively, the substrate with its ternary sandwich immune complex can be washed and then the anti-MEP antigen antibody portion of the complex is detected by means well known in the art. For example, a labeled anti-anti-MEP antibody can be used; if the anti-MEP antibody was raised in species A (a rabbit for example), then a labeled anti-A antibody raised in a different species (i.e., mouse anti-rabbit) could be used to detect the anti-MEP in the ternary complex. Other labeled specific binding proteins that bind to the anti-MEP antibody can be used, such as protein A. The most preferred method of detecting the exported antigens uses F(ab')$_2$ fragments made from the anti-vesicle antibodies bound to an inert solid substrate, an unlabeled anti-MEP IgG antibody and labeled protein A for detection. The results of Example 1 support the discussions and conclusions referred to hereinabove.

The present invention has proven effective for use with urine, blood, and tissue biopsies from mammals, and with crushed ticks. The use of pooled polyclonal, instead of monoclonal, antibodies reduces loss of recognition caused by genetic and antigenic variation among *B. burgdorferi* isolates. Furthermore, the sensitivity of this system for antigen detection in titered urine is at least $10^4$ times greater than reported by the 3M study. This conclusion is based upon the findings of the present inventors when urine is diluted 1:2 million and upon the report of a dilution of 1:64 (Hyde, F. W. et al (1989), Detection of antigen in urine of mice and humans infected with *Borrelia burgdorferi*; etiologic agent of Lyme disease, J. Clin. Microbiol. 27:58-61).

Accordingly, the present invention relates to a method for detecting the presence of specified microorganisms in a sample, which comprises capturing *Borrelia burgdorferi* antigens in said sample with F(ab')$_2$ fragments, F(ab) fragments or with intact or untreated antibody molecules (e.g., IgG or IgM) raised against the extracellular membrane vesicle exported from *Borrelia burgdorferi*: and contacting the captured antigens with polyclonal antibodies raised against the 83 kDa MEP. The capture and contact of the antigens and antibodies may occur in physiological saline such as dPBS. In addition, the *Borrelia burgdorferi* antigens in said sample may be captured with immobilized F(ab')$_2$ fragments, immobilized F(ab) fragments or immobilized intact antibody molecules capable of binding *Borrelia burgdorferi* antigens. The polyclonal antibodies may be radioactively labeled and the resulting antigen/IgG complex may readily be detected by radioimmunoassay (Gee, A. P. and J. J. Langone (1983), Immunoassay using antigen-coated plastic tube on radiolabeled or enzyme labeled Protein A, Methods Enzymol. 92:403-413; Umetsu, D. T., R. S. Geha (1987), In vitro production of antibody in cultures of human peripheral blood lymphocytes. Methods Enzymol. 150:309-316). Alternatively, the polyclonal antibodies may be contacted with a reagent (e.g., labeled) capable of reacting with polyclonal antibodies and the antibody/reagent complex is then detected. For instance, the antibody/reagent complex may be visually detected through a microscope.

Preferably, the polyclonal antibodies are of IgG class and a reagent capable of reacting with polyclonal IgG is a Protein A conjugate, such as manufactured by Sigma Chemical Company, St. Louis, Mo. (e.g., Protein A gold, Catalog No. P1039). Other suitable reagents capable of reacting with IgG include commercially available Protein G conjugates or similar anti-IgG antibody conjugates. Protein G gold conjugates are available from Sigma Chemical Co., St. Louis, Missouri, Catalog No. P1671.

Although the polyclonal antibodies of the invention are preferred, a system containing various monoclonal antibodies functioning as a polyclonal system is also within the scope of the present invention.

The use of the term "F(ab')$_2$ fragments" when describing reagents for the specific capture of *Borrelia burgdorferi* antigens encompasses the use of "F(ab) fragments" or intact antibodies for this purpose.

Various samples can be tested for the presence of bioproducts indicative of the presence of Lyme disease spirochete in unknown biological samples by the method of the present invention. For diagnosis of Lyme disease a body sample from a patient suspected of being infected will normally be diluted in an appropriate solution such as physiological saline and this solution will then be contacted with the diagnostic device containing the substrate and the immobilized F(ab')$_2$ fragments. Then, the antigen is detected with polyclonal IgG raised against the 83 kDa MEP and a reagent capable of reacting with polyclonal IgG such as a Protein A conjugate. When testing for the presence of bioproducts indicative of the presence of the Lyme disease spirochete in, for instance, the blood of a patient to be tested, the blood is drawn from the patient in a routine manner and the blood is then optionally placed in a sterile solution. This solution will then be tested for the presence of bacteria. The biological sample may comprise mammalian urine, blood or organs. The organ may be selected from the group consisting of macerated urinary bladder, spleen, liver, heart, kidney and brain tissue. The sample may also comprise an ixodid tick.

Various insoluble substrates to which the F(ab')$_2$ fragments can be bound may be used. The substrate should be capable of easily binding the F(ab')$_2$ fragments without interfering with the d agnostic test to be conducted. Possible substrates include glass; thin layer chromatographic materials such as silica gel; synthetic plastic materials such as polyvinyl chloride, polystyrene, polypropylene and polyethylene. The substrates may be in the form of flat plates, glass beads, thin layers on another substrate, microtiter plates, Petri dishes, latex beads, agarose or other types of beads, filter paper, nylon filter membranes, bacterial or other types of cells, glass slides, glass tubes, plastic tubes, etc. The substrate may also be in the form of a membrane or film of either a porous or nonporous nature. Preferably, the F(ab')$_2$ fragments may be immobilized to a solid surface selected from the group consisting of Parlodion-coated electron microscopy grids, nitrocellulose filter membranes, glass cover slips and microtiter wells.

The F(ab')$_2$ fragments should be bound to the substrate in an amount sufficient to and in a manner which allows binding of the antigens to be detected to the F(ab')$_2$ fragments. From a practical point of view, the F(ab')$_2$ fragments will usually be present in an amount of at least 0.1 ng/mm$^2$, more preferably at least 1-1.7 ng/mm$^2$ of surface area of the substrate. As far as the upper limit of the concentration of the F(ab')$_2$ fragments on the substrate, the F(ab')$_2$ fragments can be bound up to the saturation density of the substrate. For instance, the saturation density of F(ab')$_2$ fragments on polystyrene is established in a routine manner for a given manufacturers substrate (Engvall, E. and P. Perlmann (1972), Enzyme-linked immunosorbent assay, ELISA III, Quantification of specific antibodies by enzyme-labeled anti-immunoglobulin in antigen coated tubes, J. Immunol. 109:129–135; Voller A., D. Bidwell, G. Huldt, and E. Engvall (1974), A microplate method of enzyme-linked immunosorbent assay and its application to malaria, Bull. Wld. Hlth. Org. 51:209–211). The F(ab')$_2$ fragments can be bound as a molecular monolayer which substantially completely covers the surface area of the substrate. Use of more than a molecular monolayer of F(ab')$_2$ fragments bound to the substrate may result in a waste of materials and may result in inefficient binding of the F(ab')$_2$ fragments to the substrate. Preferably, the substrate is saturated with the F(ab')$_2$ fragments after experimentally determining the optimal quantity of F(ab')$_2$ fragments to use with a given substrate.

The F(ab')$_2$ fragments may be bound to the substrate in any suitable manner. Covalent or non-covalent (e.g., hydrophobic) bonding may be used to bind the F(ab')$_2$ fragment to a substrate. Alternatively, F(ab')$_2$ fragments may be covalently bonded to a substrate. Other forms of bonding such as ionic bonding may be used. Intact antibody molecules or F(ab) fragments may be substituted for F(ab')$_2$ fragments provided the substituted reagents can retain *Borrelia burgdorferi* antigens on the substrate, without causing non-specific cross-reaction with the detection reagents described herein.

The F(ab')$_2$ fragments may also be bound to particles, such as latex particles, which are thereafter immobilized by imbedding in or binding to a porous membrane. The latex particles may be of a size which can be embedded by pressure into the pores of the porous membrane. Thus, for example, the average particle size of the latex particles may be about the same as, or slightly smaller than, the average surface pore size of said porous membrane. Alternatively, the particles may be bound to any porous or liquid permeable material such as a screen, net, etc. A material such as a binder may be used to bind the particles to the support as long as the binder does not interfere with the ability of the F(ab')z fragments to bind microorganisms.

The sample suspected of containing *Borrelia burgdorferi* or its exported antigens is contacted with the substrate containing the F(ab')$_2$ fragments described hereinabove. Preferably, the solution is contacted with the substrate until or before equilibrium is reached, e.g., 10 to 120 minutes, more preferably 30 to 60 minutes at a temperature of 20° to 37° C., preferably 25° to 37° C. The precise time and temperature conditions are selected to provide sufficient time for the bacterial antigens to adsorb to the F(ab')$_2$ fragments to a degree sufficient to allow for accurate testing. The sample to be tested may be dissolved and/or diluted with various liquids such as physiological saline, etc.

After the solution has been contacted with the substrate containing the F(ab')$_2$ fragments for a time sufficient to allow the bacteria or antigens exported by the bacteria to bind to the F(ab')$_2$ fragments, the substrate is optionally washed to remove all unbound materials.

A test is then conducted to determine the presence of the 0 bacteria or antigens exported by the bacteria bound to the F(ab')$_2$ fragments on the substrate. Various tests to accomplish this purpose are known in the art such as the enzyme linked immunosorbent assay (ELISA), a radioimmune assay test, direct or indirect fluorescent antibody test, etc. Basically, the substrate containing the F(ab')$_2$ fragments and suspected of containing bacterial antigen bound thereto is contacted with a material which binds to the bacterial antigen to be tested. Such materials include, for example, antibodies against the bacterial antigen (e.g., polyclonal IgG). The substrate/F(ab')$_2$ fragment/antigen/polyclonal IgG complex is labeled with a reagent capable of reacting with polyclonal IgG such as Protein A conjugates, Protein G conjugates, etc.

Reagents such as Protein A may be "labeled" with a substance which may be easily detected. For example, the Protein A may be conjugated with an enzyme, radioactive material or element or fluorescent material. If the Protein A is conjugated with an enzyme, the substrate is thereafter contacted with a substrate for the enzyme which preferably turns color upon contact with the enzyme thereby indicating a positive reaction. The Protein A to be used should be one which reacts with the polyclonal IgG but which does not react with the F(ab')$_2$ fragments bound to the substrate thereby preventing a false positive reading. If the Protein A is radioactively labeled, then the presence of radioactivity on the substrate should be measured. It is also possible that the Protein A may be fluorescently labeled. In this situation the treated substrate should be exposed to ultraviolet light to determine the presence of the fluorescent labeled material bound to the substrate. Preferably, the Protein A conjugates may be selected from the group consisting of colloidal gold, fluorescent materials such as fluorescein isothiocyanate, rhodamine, latex beads or other suitable beads, biotin, avidin, enzymes such as horseradish peroxidase and alkaline phosphatase. Other suitable reagents capable of reacting with polyclonal IgG include Protein G conjugates, similar anti-IgG antibody conjugates and direct conjugates with anti-MEP IgG, or F(ab) or F(ab')$_2$ fragments made from anti-MEP IgG.

The detection system of the invention has proven effective at detecting antigen in mouse urine diluted 1:2,000,000 in dPBS (physiological saline).

The present invention is further directed to a diagnostic kit for detecting the presence of Borrelia burgdorferi or exported antigens, comprising F(ab')$_2$ fragments, F(ab) fragments or intact or untreated antibody molecules, capable of capturing and retaining Borrelia burgdorferi antigens; polyclonal antibodies raised against the 83 kDa MEP, these antibodies may be directly labeled or a labeled specific binding protein that specifically binds the polyclonal antibodies is used with polyclonal IgG (e.g., Protein A conjugates) and capable of detecting the presence of antigen-antibody complex. For example, the F(ab')$_2$ fragments, F(ab) fragments or intact antibody molecules are capable of being immobilized on a support optionally supplied with the test kit.

Accordingly, the kit for diagnosing Lyme disease may comprise a) anti-MEP antibodies or b) labeled anti-MEP antibodies c) anti-MEP antibodies and labeled anti-anti-MEP antibodies or labeled protein A or d) anti-vesicle antibodies and anti-MEP antibodies, etc.

The F(ab')$_2$, F(ab) fragments, intact antibody molecules capable of binding Borrelia burgdorferi antigens, IgG preparations and reagents capable of reacting with polyclonal IgG such as Protein A conjugates may be in the form of a powder.

The present invention is also directed to a method of diagnosing Lyme disease in a mammal (e.g., human and domestic animals such as dogs, cats, horses, goats, sheep, cows, etc.) comprising the steps of taking a biological sample suspected of containing Borrelia burgdorferi antigens from a mammalian (e.g., human) host, capturing Borrelia burgdorferi antigens in said sample with F(ab')$_2$ fragments, F(ab) fragments or with intact antibody molecules raised against the extracellular membrane vesicles; and detecting the antigen with polyclonal antibodies raised against the 83 kDa MEP antigen. The biological sample comprises, for instance, mammalian urine, blood or organ. The organ is selected from the group consisting of macerated urinary bladder, spleen, liver, brain tissue, heart and kidney.

In addition, the present invention can be used to determine whether ixodid ticks contain Borrelia burgdorferi. For example, the tick may be crushed in Dulbecco's phosphate-buffered saline pH 7.2 (dPBS) and used as the sample to be detected in the method of the present invention.

Moreover, the present invention is directed to an antigen comprising purified major extracellular protein antigen isolated from Borrelia burgdorferi. Extracellular membrane vesicles were recovered from log phase cultures of Borrelia burgdorferi as described by Garon, et al. (1989) Structural features of Borrelia burgdorferi—the Lyme disease spirochete: silver staining for nucleic acids. Scanning Microscopy Supplement 3, pages 109-115. Cells were removed from the cultures by centrifugation at 20° C., for 20 min, at 10,000×g. Cell removal was assured by further centrifugation for 15 min, at 20,000×g, and by filtration through a 0.22 μm filter. Vesicles were recovered from this filtrate by centrifugation for 1 hr at 257,000×g, at 20° C. Vesicle pellets were resuspended in dPBS, then layered onto a 10-70% step sucrose gradient in dPBS, and centrifuged for 2 hr at 259,000×g at 4° C. Banded membranes were then removed, diluted 1:1 in dPBS, and collected by centrifugation for 15 min at 435,000×g at 4° C.

Such vesicles, when suspended at 1 μg per ml of dPBS, were used as immunogens in rabbits. Antibodies produced by rabbits immunized with vesicles were used to produce "anti-vesicle F(ab')$_2$ fragments." These vesicles were also used as a source from which a "MEP" antigen was purified.

Accordingly, the present invention is further directed to antigens of extracellular vesicles isolated by the steps of removing cells from Borrelia burgdorferi cultures by fractionation, for example, by centrifugation, filtering the cells and collecting a filtrate, recovering the vesicles from the filtrate, layering the vesicles on a sucrose gradient, and removing banded membranes from the sucrose gradient.

A major extracellular protein (MEP) antigen was purified electrophoretically from extracellular vesicle extracts, separated by sodium dodecylsulfate-polyacrylamide gel electrophoresis (Judd, R. C. (1988) Purification of outer membrane proteins of the Gramnegative bacterium Neisseria gonorrhoeae. Anal. Biochem. 173:307-316). The MEP antigen is a protein with an apparent molecular mass of 83 kilodaltons (kDa), and it is shown in FIG. 1. It constitutes the major protein component of purified extracellular vesicles (as described above). The function of the MEP antigen is unknown, however preliminary data suggests that the surface or s-layer of Borrelia burgdorferi is primarily made of the MEP antigen.

The purification of the MEP antigen is set forth in Example 1, and it was used to immunize rabbits as described in Example 1. Polyclonal IgG produced by rabbits, in response to this protein was used as a detection reagent for the diagnostic test.

The present invention is further directed to an antibody raised against the antigens described above. For example, the invention is directed to anti-vesicle F(ab')$_2$ fragments which have a molecular mass of approximately 95 kDa. They have an antigen-binding valence of 2, meaning that they can bind (immobilize) two moles of antigen per mole of F(ab')$_2$. For example, a 1 µg/ml solution of F(ab')$_2$ fragments would contain approximately 10.5 picomoles, capable of binding up to 21 picomoles of antigen.

The F(ab')$_2$ fragments were made by digestion of anti-vesicle IgG with pepsin, followed by affinity chromatography, as described in Example 1. The IgG was accordingly purified from anti-vesicle serum by affinity chromatography with Protein A-agarose, as described in Example 1. The F(ab')$_2$ fragments can bind and immobilize cell-surface and extracellular antigens produced by *Borrelia burgdorferi*, and they were used for such a purpose in this invention.

Moreover, the present invention is further directed to polyclonal antibodies raised against the 83 kDa MEP antigen. These antibodies were produced by rabbits in response to immunization with purified MEP antigen, and was purified by affinity chromatography as described in Example 1.

The anti-MEP IgG binds to the MEP, and to a protein at 31 kDa (OspA), on immunoblots (FIG. 1), and it binds to cell-surface, and extracellular antigens produced by *Borrelia burgdorferi*. It does not bind to antigens produced by related spirochetes such as other species of Borrelia, and *Leptospira interrogans*. Anti-MEP IgG is used in this invention to detect antigens produced by *Borrelia burgdorferi*, that have been captured and immobilized by the anti-vesicle F(ab')$_2$ fragments.

EXAMPLE 1

Bacteria. The bacteria used in this study are described in Table 1.

TABLE 1

Bacteria used in Example 1

| Organism | Strain | Source | Anti-MEP/ GPA |
|---|---|---|---|
| B. burgdorferi | 19678 | P. leucopus, N.Y. | + |
| B. burgdorferi | 20004 | I. ricinus, France | + |
| B. burgdorferi | 26816 | Microtus, R.I. | + |
| B. burgdorferi | B31 | I. dammini, N.Y. | + |
| B. burgdorferi | G2 | Human CSF, Germany | + |
| B. burgdorferi | HB19 | Human blood, Conn. | + |
| B. burgdorferi | Sh-2-82 | I. dammini, N.Y. | + |
| B. anserina | | RML | − |
| B. coriaceae | C053 | Ornithodoros coriaceus, Calif. | − |
| B. hermsii | HSI | O. hermsi, Wash. | − |
| B. parkeri | | RML | − |
| B. turicatae | | RML | − |
| L. interrogans | | ATCC 23581 | − |

Abbreviations: ATCC, American Type Culture Collection; GPA, Protein A-colloidal gold conjugate; MEP, major extracellular protein; RML, Rocky Mountain Laboratories collection; CSF, cerebral spinal fluid.

All bacteria from Table 1 were maintained in BSK II media described in (Barbour, A. G. 1984. Isolation and cultivation of Lyme disease spirochetes. Yale J. Biol. Med. 57:521–525). Whole cells (WC) and extracellular membrane vesicles were recovered by filtration and differential centrifugation as described in (Dorward, D. W., and R. C. Judd. 1988. The isolation and partial characterization of naturally-evolved outer membrane blebs of *Neisseria gonorrhoeae*. p. 349–356. In Gonococci and Meningococci, J. T. Poolman, H. C. Zanen, T. J. Meyer, J. E. Heckels, P. R. H. Makela, H. Smith, and E. C. Beuvery (eds.), Kluwer Academic Publishers, Dordrecht, The Netherlands and Garon, C. F., D. W. Dorward, and M. D. Corwin. 1989. Structural features of *Borrelia burgdorferi*—the Lyme disease spirochete: silver staining for nucleic acids. Scanning Microscopy Supplement 3, pages 109–115).

Antibodies. Polyclonal rabbit sera were raised against membrane vesicles and the 83 kDa MEP, electrophoretically purified from vesicles (Dorward, D. W., and R. C. Judd. 1988. The isolation and partial characterization of naturally-evolved outer membrane blebs of *Neisseria gonorrhoeae*. p. 349–356. In Gonococci and Meningococci, J. T. Poolman, H. C. Zanen, T. J. Meyer, J. E. Heckels, P. R. H. Makela, H. Smith, and E. C. Beuvery (eds.), Kluwer Academic Publishers, Dordrecht, The Netherlands and Judd, R. C. 1988. Purification of outer membrane proteins of the Gramnegative bacterium *Neisseria gonorrhoeae*. Anal. Biochem. 73:307–316). Emulsions of antigen, and monophosphorylated lipid A and trehalose dimycolate (Ribi ImmunoChem, Inc., Hamilton, Mont.) were prepared according to manufacturer's instructions and used as primary immunogens. Immunized rabbits were periodically boosted with antigen suspended in dPBS. Sera were collected over a period of 10 weeks.

Immunoglobulin G (IgG) was purified from the sera by affinity chromatography with Protein A-agarose (Sigma Chemical Co., St. Louis, Mo.). Eluted IgG was dialyzed overnight with water, and lyophilized for storage.

For some experiments, F(ab')$_2$ fragments were produced from IgG, directed against vesicles, by passage through pepsin-agarose (Sigma) as described in Lamoyi, E., and A. Nisonoff, 1983, Preparation of F(ab')$_2$ fragments from mouse IgG of various subclasses, J. Immunol. Methods 56:235–243. Cleaved IgG was subsequently passed through Protein A-agarose and the void volume was retained. F(ab) fragments can be produced by passage through papain-agarose (Sigma) instead of pepsin-agarose as described above.

Experimental mouse infections. White-footed mice (*Peromyscus leucopus*) were experimentally infected with *B. burgdorferi* by intra-peritoneal injection with 0.1 ml suspensions of spirochetes in dPBS at an OD$_{600nm}$ of 0.4 (Schwan, T. G., W. Burgdorfer, and C. F. Garon. 1988. Changes in infectivity and plasmid profile of the Lyme disease spirochete, *Borrelia burgdorferi*, as a result of in vitro cultivation. Infect. Immun. 56:1831–1836 and Schwan, T. G., W. Burgdorfer, M. E. Schrumpf, and R. H. Karstens. 1988. The urinary bladder, a consistent source of *Borrelia burgdorferi* in experimentally infected white-footed mice (*Peromyscus leucopus*). J. Clin. Microbiol. 26:893–895). Urine, blood, and organs such as bladder, spleen, liver, kidney, heart and brain were collected from infected and uninfected animals. Infection was confirmed by culturing *B. burgdorferi* from triturated urinary bladders, as described in Schwan, T. G., W. Burgdorfer, and C. F. Garon, 1988, Changes in infectivity and plasmid profile of the Lyme disease spirochete, *Borrelia burgdorferi*, as a result of in vitro cultivation. Infect. Immun. 56:1831–1836 and Schwan, T.

G., W. Burgdorfer, M. E. Schrumpf, and R. H. Karstens. 1988. The urinary bladder, a consistent source of *Borrelia burgdorferi* in experimentally infected white-footed mice (*Peromyscus leucopus*). J. Clin. Microbiol. 26:893–895.

Human, canine, and tick materials. Clinical human urine and Ixodes dammini ticks, collected from Juneau County, Wis., were graciously provided by Dr. Paul Duray. Human urine samples were also provided by laboratory volunteers. Acute human serum from Southampton, N.Y., was supplied by Dr. Alan MacDonald. Whenever possible, assays on human specimens were compared with serological data and/or patient histories. Urine and blood from a dog, naturally-infected in Bridgewater, N.J., were provided by Sara Stephens, D.V.M., Missoula, Mont.

Immunoblot analysis. Antigens, precipitated from urine with anti-MEP antibodies, WC, and vesicles, were solubilized and subjected to sodium dodecylsulfate-polyacrylamide gel electrophoresis using the discontinuous buffer system of Laemmli (Laemmli, U. K. 1970. Cleavage of structural proteins during the assembly of the head of bacteriophage T4. Nature (London) 227:680–685), with the modifications described in Judd, R. C. 1982, $^{125}$I-peptide mapping of protein III isolated from four strains of *Neisseria gonorrhoeae*. Infect. Immun. 37:622–631. Separated proteins were electroblotted onto nitrocellulose, blocked with 0.05% Tween 20 in dPBS or 5% nonfat dry milk in dPBS, and probed with serum or IgG, as described in Batteiger, R., W. J. Newhall, and R. B. Jones, 1982, The use of Tween 20 as a blocking agent in the immunological detection of proteins transferred to nitrocellulose membranes, J. Immunol. Methods 55:297–307. Resulting immune complexes were labeled with Protein A-horseradish peroxidase, and detected by chromogenic assay.

Electron microscopy. Copper grids were coated with Parlodion, then incubated for 10 min, at room temperature, on a 6 µl droplet of anti-vesicle F(ab')$_2$ fragments dissolved at 1 µg per ml of dPBS. The grids were washed twice for 10 min with dPBS, then incubated for 10 min on a 6 µl droplet of antigen prepared as follows: urine, diluted 1:10 or as specified in dPBS; blood, diluted 1:10 in dPBS; and ticks or mouse organs such as bladder, spleen, liver, kidney, heart and brain, macerated in an equal volume of dPBS in glass tissue grinders. Following two, 10 min washings in dPBS, the grids were transferred onto 6 µl droplets of anti-MEP IgG and incubated at room temperature for 20 min. Two more dPBS washings were done, then antigen-antibody complexes were labeled for 20 min with 6 µl of Protein A-colloidal gold conjugates, prepared by the methods of Robinson and co-workers (Robinson, E. N., Z. A. McGee, J. Kaplan, M. E. Hammond, J. K. Larson, T. M. Buchanan, and G. K. Schoolnik. 1984. Ultrastructural localization of specific gonococcal macromolecules with antibody-gold sphere immunological probes. Infect. Immun. 46:361–366). The grids were washed twice for 5 min each in dPBS, twice for five min each in 0.25M ammonium acetate, then negatively stained with 0.5% ammonium molybdate, pH 6.5. The grids were dried in air, and observed at 75 kV with a model HU-11E-1 transmission electron microscope (Hitachi, Ltd., Tokyo, Japan).

RESULTS

To address whether membrane vesicles are released by *B. burgdorferi* in vivo, polyclonal rabbit antibodies were raised against vesicles and the 83 kDa MEP antigen. After purification from collected sera, IgG from the rabbits was screened for reactivity with WC and vesicles by immunoblot analysis (FIG. 1). In FIG. 1, electroblotted whole cell (WC) and vesicle proteins were stained with buffalo black (B. black), probed with polyclonal rabbit IgG generated against extracellular vesicles or the 83 kilodalton major extracellular protein antigen (MEP), or probed with the anti-OspA monoclonal antibody, TS-2. Anti-vesicle IgG recognized several WC and vesicle proteins, including OspA and OspB. The anti-MEP IgG recognized a 31 kilodalton protein, corresponding to OspA in WC and vesicle lanes. Accordingly, blotted proteins were either stained with buffalo black, or probed with anti-vesicle, polyclonal anti-MEP, or monoclonal anti-OspA antibodies, then labeled and detected as described above. Numerous WC and vesicle proteins were recognized by anti-vesicle IgG. Polyclonal IgG from rabbits immunized with the MEP, reacted primarily with a 31 kDa protein corresponding to OspA by electrophoretic migration. Only minimal labeling of the 83 kDa immunogen occurred. Reaction with monoclonal antibody TS-2 (Rocky Mountain Laboratories Collection) confirmed the presence of OspA in WC and vesicles.

Figure 2A:
FIGS. 2a through 2c show localization of epitopes recognized by IgG directed against the major extracellular protein antigen (MEP).
Figure 2B:
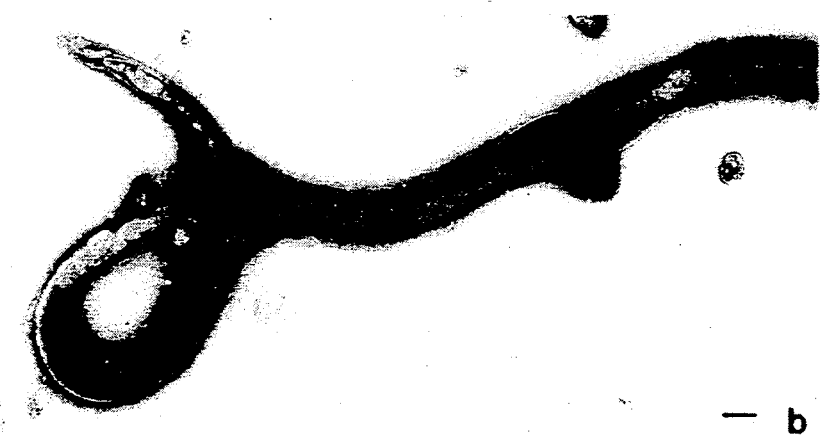
Figure 2C:

To determine whether these polyclonal sera could be used to concentrate and specifically detect intact WC and elaborated vesicles, Parlodion-coated electron microscope grids were adsorbed with F(ab')$_2$ fragments made from anti-vesicle IgG. Such "activated" grids were incubated either with in vitro cultures of *B. burgdorferi* or with media alone. Antigens adhering to the grids were detected with anti-MEP IgG and Protein A-colloidal gold conjugates (FIG. 2). FIG. 2 describes the parlodion-coated grids were activated with anti-vesicle F(ab')$_2$ fragments, then incubated with cultured *B. burgdorferi* cells (2a, b) or with culture media (2c). The grids were then probed with anti-MEP IgG (2a, c) or pre-immune serum (2b), labeled with Protein A-colloidal gold conjugates, and examined by electron microscopy. Gold particles adhered to cell and vesicle surfaces and to flocculent material surrounding cells. Only background levels of gold were observed on grids incubated with media, or probed with pre-immune serum. Bars, 200 nm. Both WC and vesicles adhered to activated grids. Heavy labeling was evident on the surfaces of cells and vesicles, and on flocculent material surrounding these structures. Sparse deposition of gold on the control grids lacking antigen, or incubated with pre-immune serum, was considered non-specific background.

To determine the specificity of the anti-MEP polyclonal IgG seven strains of *B. burgdorferi*, five other Borrelia species, and *Leptospira interrogans* (Table 1) were assayed. All seven *B. burgdorferi* isolates from the U. S. and Europe were specifically labeled, whereas the other spirochetes retained only background levels of gold.

Activated grids were then incubated with possible in vivo sources of *B. burgdorferi* antigens to assess the possibility of adapting this system to clinical samples. The samples tested included macerated Ixodes sp. ticks, specimens of urine, blood, or macerated tissues from mice, dogs, and humans (FIGS. 3, 4).

FIG. 3 discloses the immune electron microscopic detection of *B. burgdorferi* antigens in mammalian urine and blood. Parlodion-coated grids were activated with anti-vesicle F(ab')$_2$ fragments, incubated with urine or blood samples, probed with anti-MEP IgG, and labeled with Protein A-colloidal gold conjugates. Heavily-labeled flocculent antigens were aggregated on grids incubated with urine from infected mice, dogs, and humans (3a, c, d, respectively), and with blood from infected mice (3b). Labeled membrane vesicles were occasionally observed (3a, insert). No specific labeling was observed in urine and blood from uninfected mice (3e, f). Bars, 200 nm.

Figure 3A:
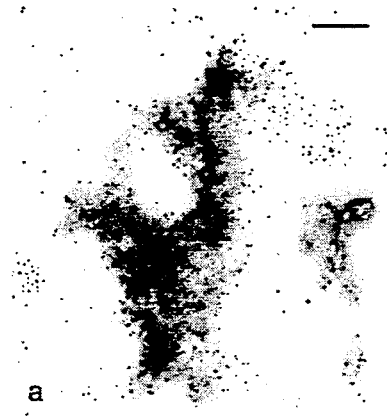
FIGS. 3a through 3f show immune electron microscopic detection of *B. burgdorferi* antigens in mammalian urine and blood.
Figure 3B:
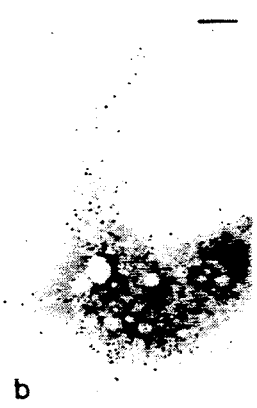
Figure 3C:
Figure 3D:
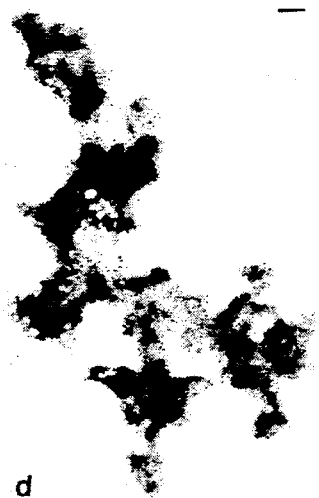
Figure 3E:
Figure 3F:
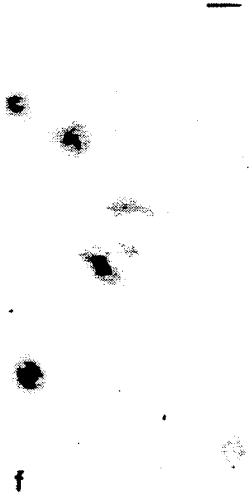
Figure 4A:
FIGS. 4a through 4h show detection of *B. burgdorferi* antigens in macerated ixodid ticks and mouse tissues.
Figure 4B:
Figure 4C:
Figure 4D:
Figure 4E:
Figure 4F:
Figure 4G:
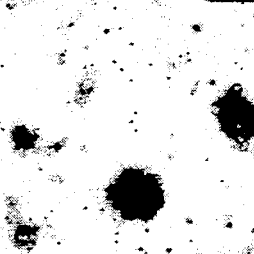
Figure 4H:

Capture and labeling of flocculent antigen was evident in urine and blood of five experimentally-infected mice (3a, b). Some fields contained labeled membranous structures resembling vesicles (FIG. 3a, insert). Similar flocculent material was evident in urine from a naturally-infected dog (3c) and a clinical human patient (3d). Labeled flocculent antigen was detected in mouse urine diluted up to $2 \times 10^6$ in dPBS. No evidence of material, specifically labeled with gold, was detected in samples from uninfected mice or humans (3e, f). A total of 39 human urine samples were tested. These included two negative samples provided by laboratory personnel, and 37 clinical samples from patients suspected of having Lyme disease. A single clinical sample was negative, while 36 had aggregates of flocculent antigen.

The macerated tissues examined included ticks, urinary bladder, spleen, liver, heart, brain, and kidney (FIGS. 4a–g, respectively). FIG. 4 discloses the detection of B. burgdorferi antigens in macerated ixodid ticks and mouse tissues. Electron microscope grids were activated, incubated with macerated tissue, and precipitated antigens were labeled with anti-MEP IgG and Protein A-colloidal gold conjugates. When examined, flocculent antigens were observed on grids incubated with infected Ixodes dammini ticks, and urinary bladder, spleen, liver, heart, and brain from infected *Peromyscus leucopus* (4a–f, respectively). Infected *P. leucopus* kidney had relatively dense labeling, but antigen aggregates were not observed on such grids (4g). Little gold was observed on control grids lacking antigen (4h). Bars, 200 nm. All but kidney specimens contained flocculent antigen. Although, kidney tissue was labeled more densely than control grids, antigen aggregates were not resolved. However, intact spirochetes were found on grids incubated with bladder tissue from four of five mice examined (4b, insert). Spirochetes were also observed in the blood and spleen of a single mouse at 12 days post-infection (data not shown). Only background levels of gold were observed on control grids lacking antigen (4h).

Figure 5:
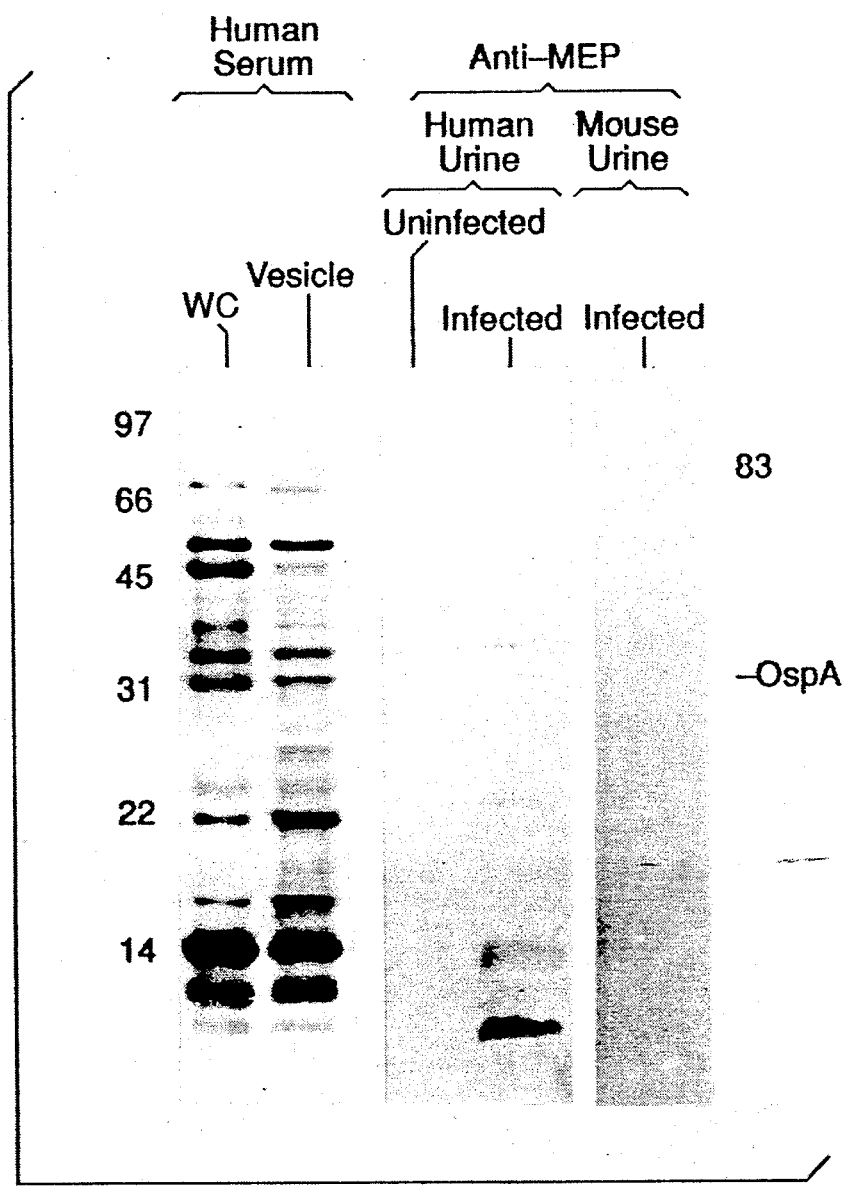
FIG. 5 shows immunoblot analysis of *B. burgdorferi* antigens, precipitated from infected mouse and human urine.
Figure 6:
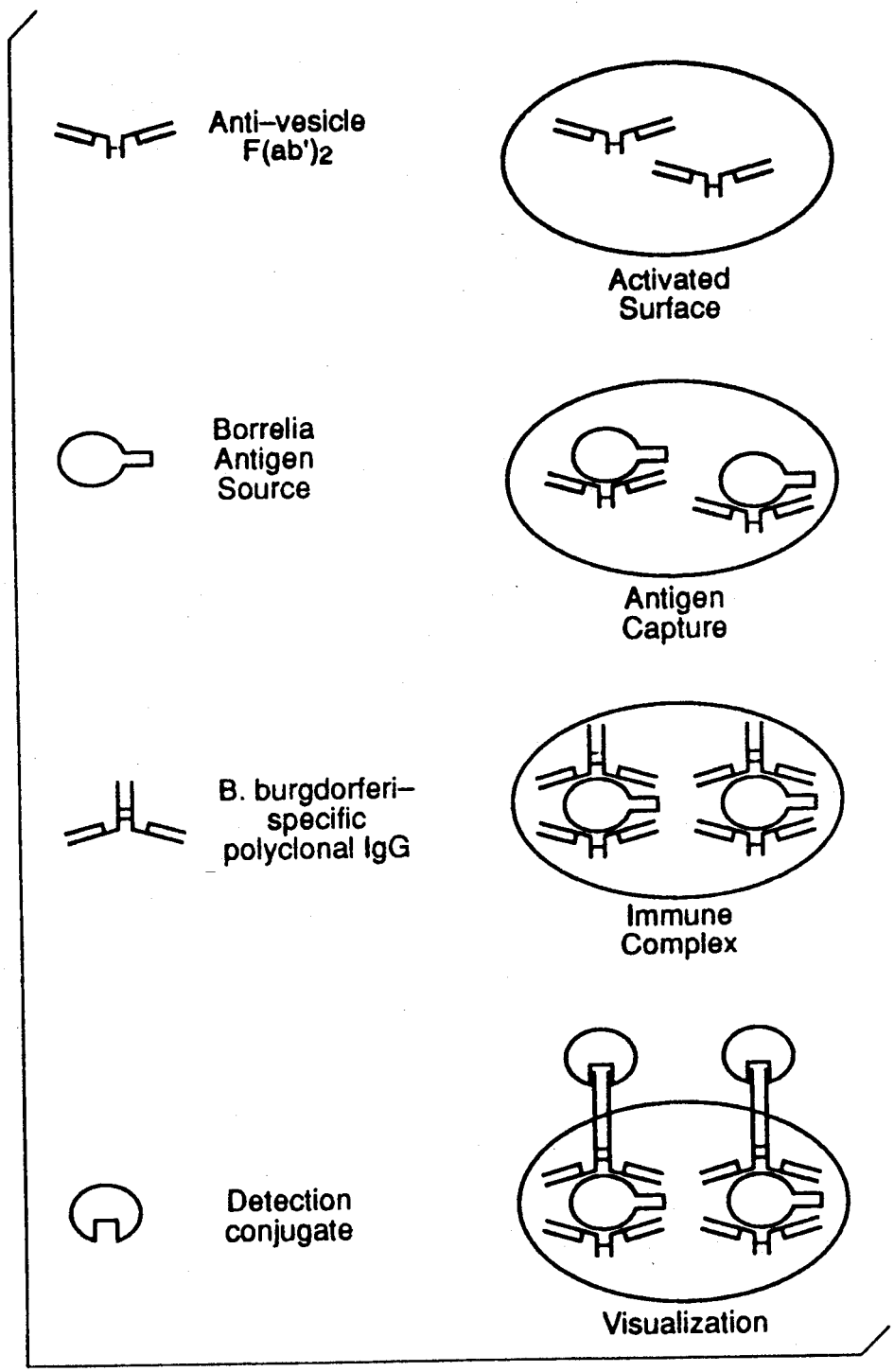
FIG. 6 shows immune capture and detection of B. burgdorferi antigens.

To identify antigens detected in urine from humans and mice, the samples were incubated with anti-MEP IgG, and resulting precipitants were recovered and compared to WC and vesicle antigens by immunoblot analysis (FIG. 5). FIG. 5 discloses immunoblot analysis of B. burgdorferi antigens, precipitated from infected mouse and human urine. The banding patterns of whole cell (WC) and vesicle antigens, detected with acute human serum, was compared with immunoblots containing antigens, precipitated from human and mouse urine with anti-MEP IgG and detected by solid phase ELISA with anti-MEP IgG. At least five bands at 34, 31, 22, 14, and 11 kilodaltons were revealed in human urine precipitants, whereas a single band at 83 kilodaltons was detected in infected mouse preparations. When blotted WC and vesicle antigens were probed with acute human serum, numerous bands were resolved. No antigens were detected in urine from two uninfected humans (data not shown). However, the anti-MEP antibody recognized at least five bands ranging from 11–34 kDa in the urine precipitant from an infected human, and an 83 kDa band was detected in the mouse urine sample. These bands all corresponded by electrophoretic migration to WC and vesicle antigens observed with acute human serum.

EXAMPLE 2

As a primary source of reagents, *Borrelia burgdorferi* strain SH-2-82 is maintained, at low passage, in BSK II medium. Extracellular membrane vesicles are recovered by filtration and differential centrifugation of cultures, for use in antibody development.

For use in concentrating and detecting Lyme antigens, polyclonal rabbit sera are raised against membrane vesicles and a 83 kDa protein electrophoretically purified from the vesicles. Immunized rabbits are periodically boosted with antigen suspended in Dulbecco's phosphate-buffered saline pH 7.2 (dPBS). Sera raised against each immunogen are collected and pooled. Immunoglobulin G (IgG) is purified from the pooled sera by affinity chromatography with Protein A-agarose. Eluted IgG is either dialyzed overnight with water and lyophilized for storage, or used directly.

Anti-vesicle IgG is processed further as follows: $F(ab')_2$ fragments are produced from IgG directed against vesicles by passage through pepsin-agarose. Digested IgG is then passed through Protein A-agarose and the void volume is retained. The anti-vesicle $F(ab')_2$ fragments are then adsorbed to a solid surface, appropriate for subsequent incubation with a biological sample. Such surfaces include, but are not limited to, Parlodion-coated electron microscopy grids, nitrocellulose filter membranes, glass cover slips, and microtiter wells. These steps provide an "activated" support for the capture and concentration of Borrelia antigens from a test sample. These steps also remove the Fc piece from the anti-vesicle IgG, that would interfere with the antigen detection procedures described below.

Fresh or refrigerated blood or urine is diluted from 1:10 to 1:100 in Dulbecco's phosphate-buffered saline at pH 7.2 (dPBS). Tissue biopsies or ticks are macerated with a tissue grinder in 1–10 ml of dPBS per gram of specimen. Test samples are then incubated for 10–30 min at room temperature in contact with the $F(ab')_2$-coated support. During this incubation, Borrelia antigens, if present, are removed from the sample and retained on the activated support. The support is then washed twice for 10 min in dPBS.

Anti-83 kDa IgG is reconstituted at 50 $\mu$g per ml of dPBS, placed in contact with supports containing test or control specimens, and incubated for 10–30 min at room temperature. Unbound IgG is removed by two 10 min washes in dPBS. The presence of antigen-antibody complexes on the supports is detected with Protein A conjugates, that bind specifically to the Fc portion of the IgG. Commercially-available conjugates appropriate for various assay systems include: colloidal gold for electron microscopy and visual chromogenic assays, fluorescein isothiocyanate or rhodamine for fluorescent microscopy, latex beads for light microscopy, and horseradish peroxidase and alkaline phosphatase for enzyme-linked immunosorbent assays (ELISA) with visual or light microscopic screening.

EXAMPLE 3

Method of Purifying Extracellular Membrane Vesicles

Extracellular membrane vesicles are recovered from log phase cultures of *Borrelia burgdorferi* as described by Garon, et al. (1989) Structural features of *Borrelia burgdorferi*—the Lyme disease spirochete: silver staining for nucleic acids, Scanning Microscopy Supplement 3, pages 109–115. Cells are removed from the cultures by centrifugation at 20° C., for 20 min, at 10,000×g. Cell removal is assured by further centrifugation for 15 min, at 20,000×g, and by filtration through a 0.22 μm filter. Vesicles are recovered from this filtrate by centrifugation for 1 hr at 257,000×g, at 20° C. Vesicle pellets are resuspended in dPBS, then layered onto a 10–70% step sucrose gradient in dPBS, and centrifuged for 2 hr at 259,000×g at 4° C. Banded membranes are then removed, diluted 1:1 in dPBS, and collected by centrifugation for 15 min at 435,000×g at 4° C.

Such vesicles, when suspended at 1 μg per ml of dPBS, are used as immunogens in rabbits. Antibodies produced by rabbits immunized with vesicles are used to produce "anti-vesicle F(ab')$_2$ fragments." These vesicles are also used as a source from which a "MEP" antigen is purified.

EXAMPLE 4

Method of Purifying MEP

Sodium dodecylsulfate extracts of purified extracellular vesicles are loaded onto preparative 12.5% polyacrylamide gels and electrophoresed for 2.5 hr at 7.5 watts, constant power. The gels are then stained with 0.25% Coomassie brilliant blue in water, and the MEP protein is identified by electrophoretic migration (the MEP protein band is the largest and darkest by far) and excised from the gel. The excised gel fragment is then loaded onto a 7.5% preparative polyacrylamide gel and electrophoresed as described above. Proteins contained in the second gel are electroblotted onto nitrocellulose membranes and stained with 1% buffalo black in water. The segment of each membrane containing the MEP is excised and boiled in two changes of 200 μl of 10% SDS to elute the protein. The protein is then precipitated with acetone, and recovered by centrifugation for 30 min at 100,000×g, and 4° C.

All publications cited hereinabove are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. Purified antibodies or antigen-binding fragments of said antibodies raised against a purified major extracellular protein antigen which is exported from *Borrelia burgdorferi*, said purified major extracellular protein antigen having a molecular weight of 83 kilodaltons (kDa).

2. The isolated antibodies or antibody fragments of claim 1, wherein said antibodies are polyclonal.

3. The antibodies or antibody fragments of claim 1, wherein said antibodies are monoclonal.

4. The antibodies or antibody fragments of claim 1, wherein said antibodies are labeled with a detectable label.

5. The antibodies or antibody fragments of claim 4, wherein said detectable label is chosen from the group consisting of radioisotopes, enzymes, fluorophores and colloidal metals.

6. A method of diagnosing Lyme disease in a mammal, which method comprises:
   i) obtaining a fluid or tissue sample from said mammal,
   ii) contacting said sample with the antibodies or antigen binding fragments of said antibodies of claim 1, under conditions in which immune complexes will form between said antibodies or fragments and any antigens associated with *Borrelia burgdorferi* that may be present in said sample, and
   iii) detecting the presence of said immune complexes as a means of diagnosing Lyme disease in said mammal.

7. The method of claim 6, wherein said antibodies are labeled with a detectable label.

8. The method of claim 7, wherein said detectable label is chosen from the group consisting of radioisotopes, enzymes, fluorophores and colloidal metals.

9. Purified antibodies or antigen-binding fragments of said antibodies raised against purified extracellular membrane vesicles exported from *Borrelia burgdorferi*, said antibodies being polyclonal.

10. A method of detecting *Borrelia burgdorfer*, or *Borrelia burdorferi* exported antigens in a sample, said method comprising:
    A) providing:
       i) a fluid or tissue sample,
       ii) purified polyclonal antibodies or antigen-binding fragments of said polyclonal antibodies raised against the extracellular membrane vesicles exported from *Borrelia burgdorferi*, and
       iii) purified antibodies or antigen-binding fragments of said antibodies raised against the major extracellular protein antigen exported from *Borrelia burgdorferi*, said protein antigen having a molecular weight of approximately 83 kDa;
    B) contacting said sample with said polyclonal antibodies of step A (ii) and said antibodies of step A (iii), under conditions in which ternary immune complexes will form among said antibodies of steps A (ii) and A (iii) and any antigens associated with *Borrelia burgdorferi* that may be present in same sample; and
    C) detecting the presence of said ternary immune complexes as a means of detecting *Borrelia burgdorferi* or *Borrelia burgdorferi* exported antigens.

11. The method of claim 10, wherein said polyclonal antibodies or antibody fragments of step A(ii) are bound to a solid substrate.

12. The method of claim 11, wherein said antibodies or antibody fragments of step A(iii) are labeled with a detectable label.

13. The method of claim 12, wherein said detectable label is chosen from the group consisting of radioisotopes, enzymes, fluorophores and colloidal metals.

14. The method of claim 11, wherein said antibodies of step A(iii) are not labeled with a detectable label and step C comprises contacting said ternary immune complexes with a specific binding protein which specifically binds to said antibodies of step A(iii), said specific binding protein being labeled with a detectable label.

15. The method of claim 14, wherein said specific binding protein is an antibody or protein A.

16. The method of claim 15, wherein said detectable label is chosen from the group consisting of radioisotopes, enzymes, fluorophores and colloidal metals.

17. The method of claim 16, wherein said specific binding protein is protein A and said polyclonal antibodies or antibody fragments of step A(iii) are F(ab')$_2$ antibody fragments.

18. The method of claim 10, wherein said sample is a fluid or tissue sample taken from a mammal or a tick.

19. The method of claim 10 wherein the presence of said *Borrelia burgdorferi* or said *Borrelia burgdorferi* exported antigens is indicative of Lyme disease caused by an infection of *Borrelia burgdorferi* in said mammal.

20. A diagnostic kit comprising:
   A) purified antibodies or antigen binding fragments of said antibodies raised against the major extracellular protein antigen exported from *Borrelia burgdorferi* having a molecular weight of approximately 83 kDa, and
   B) purified polyclonal antibodies or antigen-binding fragments of said polyclonal antibodies raised against the extracellular membrane vesicles exported from *Borrelia burgdorferi*.

21. The kit of claim 20, wherein the antibodies of element B) are bound to a solid substrate.

22. The kit of claim 21, wherein the antibodies of element A) are labeled with a detectable label.

23. The kit of claim 22, wherein the detectable label is chosen from the group consisting of radioisotopes, enzymes, fluorophores and colloidal metals.

24. The kit of claim 20 further comprising a specific binding protein which specifically binds to the antibodies of element A), said specific binding protein being labeled with a detectable label.

25. The kit of claim 24, wherein said specific binding protein is an antibody or protein A.

26. The kit of claim 25, wherein said detectable label is chosen from the group consisting of radioisotopes, enzymes, fluorophores or colloidal metals.

* * * * *